United States Patent
Metzger (10) Patent No.: US 8,281,638 B2
(45) Date of Patent: Oct. 9, 2012

(54) METHOD AND APPARATUS FOR PRODUCING A PLANAR IMPLANT FOR A HUMAN OR ANIMAL BODY

(75) Inventor: Marc Christian Metzger, Kirchzarten (DE)

(73) Assignee: Synthes USA, LLC, West Chester, PA (US)

( * ) Notice: Subject to any disclaimer, the term of this patent is extended or adjusted under 35 U.S.C. 154(b) by 878 days.

(21) Appl. No.: 12/295,790

(22) PCT Filed: Apr. 5, 2006

(86) PCT No.: PCT/EP2006/003095
§ 371 (c)(1),
(2), (4) Date: Oct. 2, 2008

(87) PCT Pub. No.: WO2007/112766
PCT Pub. Date: Oct. 11, 2007

(65) Prior Publication Data
US 2010/0192661 A1    Aug. 5, 2010

(51) Int. Cl.
*B21D 37/02* (2006.01)
*B21J 13/00* (2006.01)
*A61B 17/80* (2006.01)
*A61F 2/28* (2006.01)

(52) U.S. Cl. .......... 72/413; 72/446; 606/285; 623/23.54

(58) Field of Classification Search .................... 72/413, 72/414, 478, 441, 446, 462, 481.3, 481.5; 606/285; 623/23.54, 23.53
See application file for complete search history.

(56) References Cited

U.S. PATENT DOCUMENTS

| 4,863,474 | A |   | 9/1989  | Brown et al. |
|-----------|---|---|---------|--------------|
| 5,546,784 | A | * | 8/1996  | Haas et al. ...................... 72/413 |
| 5,766,176 | A |   | 6/1998  | Duncan |
| 5,814,048 | A | * | 9/1998  | Morgan ........................ 606/283 |
| 6,008,430 | A |   | 12/1999 | White |
| 6,053,026 | A | * | 4/2000  | Nardiello et al. ............... 72/413 |
| 7,655,047 | B2| * | 2/2010  | Swords ....................... 623/23.54 |

FOREIGN PATENT DOCUMENTS

| DE | 3425002 A1       | 1/1985  |
|----|------------------|---------|
| WO | WO 02/092882 A1  | 11/2002 |
| WO | WO 03/007831 A1  | 1/2003  |

* cited by examiner

*Primary Examiner* — Dana Ross
*Assistant Examiner* — Mohammad I Yusuf
(74) *Attorney, Agent, or Firm* — Woodcock Washburn LLP

(57) ABSTRACT

The present invention relates to a method and a device for producing a planar implant (I) for a human or animal body, which planar implant (I) is preformed corresponding to a desired anatomical shape. The method comprises the following steps: making available a blank of the planar implant; making available a preforming device (V) that comprises a plurality of discrete adjustable support elements (STE) for adjusting an associated plurality of support points in accordance with the desired anatomical shape; defining the desired anatomical shape and determining corresponding settings for the support elements; adjusting the support elements in accordance with the settings determined for the desired anatomical shape; and producing the preformed implant by bending the blank onto the adjusted support elements.

14 Claims, 7 Drawing Sheets

METHOD AND APPARATUS FOR PRODUCING A PLANAR IMPLANT FOR A HUMAN OR ANIMAL BODY

PRIOR ART

The present invention relates to a method and a device for producing a flat implant for a human or animal body, which flat implant corresponds to a desired anatomical shape.

Although, in principle, they can be used for any pre-shaped, flat implant for a human or animal body, the devices of the present invention and the problems, on which they are based, are explained in relation to preformed osteosyntheses for the orbits.

Mesh or plates of titanium or other materials, for instance, are used for the surgical care of fractures in the orbit. These are available in different prototypes and thicknesses and usually are formed planar when sold.

During the operation, therefore, the surgeon must cut these meshes to size and fold and bend them, in order to imitate the desired anatomical structures. In so doing, it is not always possible to reach, clearly define and reconstruct the lower anatomical structures of the orbital apex. Moreover, the result is highly dependent on the experience of the surgeon.

If the defect in the lower part of the orbit is not bridged, the consequences are double vision (diplopia), recession of the eyeballs (enophthalmus) and mobility disorders. In the worst case, excessive manipulations at the eye or at the visual nerve during the operation can lead to blindness (amaurosis), so that meshes should not be fitted too frequently into the orbit.

The problems, on which the present invention is based, therefore generally consist of providing a method and a device for producing a flat implant, preformed to correspond to a desired anatomical shape, for a human or animal body. The implant is to have an improved replication of the structure and to represent a simplification for the surgeon.

ADVANTAGES OF THE INVENTION

The inventive method for producing a flat implant, preformed to correspond to a desired anatomical shape, for a human or animal body with the distinguishing features of claim 1, and the corresponding have the advantage over the known solutions that they make an anatomically preformed implant possible, which replaces or reconstructs the anatomical structure ideally.

With the present invention, it is achieved that the surgical reconstruction of body tissue takes place anatomically more individually, more accurately, less dangerously for the patient, time wise more efficiently, in a more standardized fashion and independently of the experience of the surgeon.

The idea, on which the present invention is based, consists therein that a preforming device is made available, which has a plurality of discrete, adjustable supporting devices for adjusting an associated plurality of associated supporting points corresponding to the desired anatomical shape and at which preforming device the pre-formed implant is formed by bending the blank into contact with the adjusted supporting devices.

For example, individual or clustered anatomical structures are reproduced by means of CT data records for the production of the preformed implant over the correspondingly adjusted supporting point surface of the preforming device.

Advantageous further developments and improvements of the respective subject matter of the invention are found in the dependent claims.

According to a preferred further development, the preform has a two-dimensional mesh structure, which is transformed by bending into a three-dimensional mesh structure.

According to a further preferred development, the adjustments for the supporting devices are determined by the following steps:

imaging a region of the body corresponding to the desired anatomical shape in a supporting point mesh;

determining the distances between a reference surface corresponding to a specified reference setting of the supporting points of the preforming device and the supporting point mesh at the supporting points in the reference surface for a specified orientation of the supporting point mesh; and setting the distances determined at the supporting devices.

According to a further, preferred development, the desired anatomical shape corresponding region of the body is imaged in a supporting point mesh by the following steps:

imaging a region of the body corresponding to a desired anatomical shape corresponding to a mathematical image in an image supporting point mesh and transforming the image supporting point mesh into the supporting point mesh corresponding to the mathematical image.

According to a further preferred development, the imaging is carried out by means of a computer tomography device.

According to a further preferred development, the preformed fined implant is a preformed osteosynthesis for the orbit.

According to a further preferred development, the supporting devices have cylindrical pin devices, the height of which can be adjusted and which are mounted at a planar plate device.

According to a further preferred development, the supporting devices are adjusted by an automatic adjusting device.

According to a further preferred development, before the bending procedure, a thin deformable sheet device or an integrally molded casing device is mounted on the adjusted supporting devices of the preforming device.

According to a further preferred development, the desired anatomical shape is specified and the corresponding adjustments for the supporting devices are determined by the following steps:

standard, desired shapes and corresponding adjustment data is entered into a database;

a standard, desired shape is selected from the database by means of one or more of the following diameters: sex, age, race, height, side of body; and the corresponding adjustments for the supporting devices are determined by means of the adjustment data record belonging to the standard desired shapes selected.

According to a further preferred development, the implant consists of titanium. Other materials or the combination of titanium with different coatings and coverings is possible. The lining of the mesh with other material compositions, such as plastic or other bio-absorbable materials is also conceivable.

DRAWINGS

Examples of the invention are shown in the drawings and explained in greater detail in the description that follows. In the drawings.

DESCRIPTION OF THE EXAMPLES

In the Figures, identical reference numbers refer to elements having the same function.

FIGS. 1a-d show layers of an orbit, recorded by computer tomography, for explaining an embodiment of the inventive method.

In a first step of this embodiment, a desired anatomical shape for a flat implant, which is to be preformed in the form of an osteosynthesis for the orbit, is to be established.

For this purpose, computer tomography recordings of different planes of the orbit are recorded in different views, as shown in FIGS. 1a-d. As will be explained later, a supporting point mesh, with the help of which the settings for a preforming device for preforming the implant can be determined, will be formed from these recordings.

DICOM data, which is visualized three-dimensionally with the help of appropriate software, is used for the present embodiment. The software, for example, permits the following views:

a three-dimensional view of the whole skull
coronal view (sections from front)
sagittal view (sections from the side).
axial view (sections in the axis)

In order to determine the bottom structure of the orbit for the present example, the healthy side of the skull is measured by computer tomography and subsequently reflected at the middle of the skull. Accurately defined points, which have a grid for which the distances between the measurement points is defined accurately, are required for the later formation of the supporting point mesh. For this purpose, the coronal and sagittal views are used in order to mark layers at a defined distance. The marking can be made by means of Houndsfield units, which reproduced the different gray values of the computer tomogram automatically by gray value definition or manually by means of a brush tool.

When layers are marked in the coronal view, the area of the front edge of the orbit of the orbit is available as the starting layer. For example, each layer has a thickness of 0.5 mm. A resolution can be specified by selecting or skipping certain layers. In that case of the example, the highest resolution is an interval of 0.5 mm between layers and the least resolution can be defined individually by a multiple of the interval of 0.5 mm between layers.

When layers are marked in the sagittal view, the region of the side edge of the orbit is available as starting layer. Preferably, the same interval between layers is used as for the coronal view.

Figure 1A:
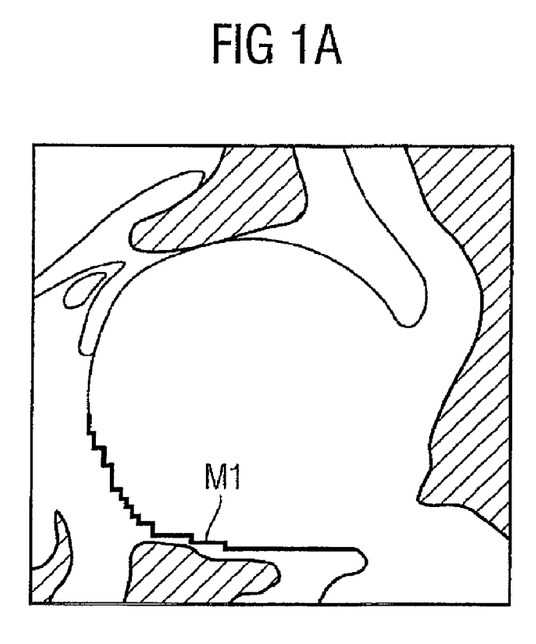
FIGS. 1*a-d* show layers of an orbit, recorded by computer tomography, to illustrate an embodiment of the inventive method.
Figure 1B:
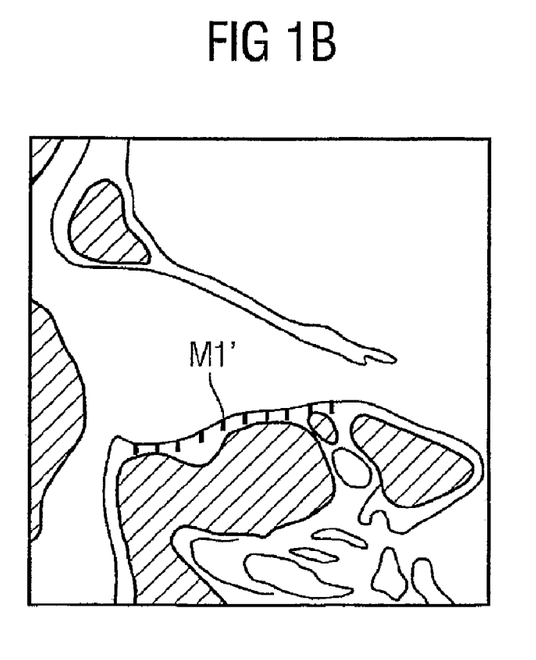
Figure 1C:
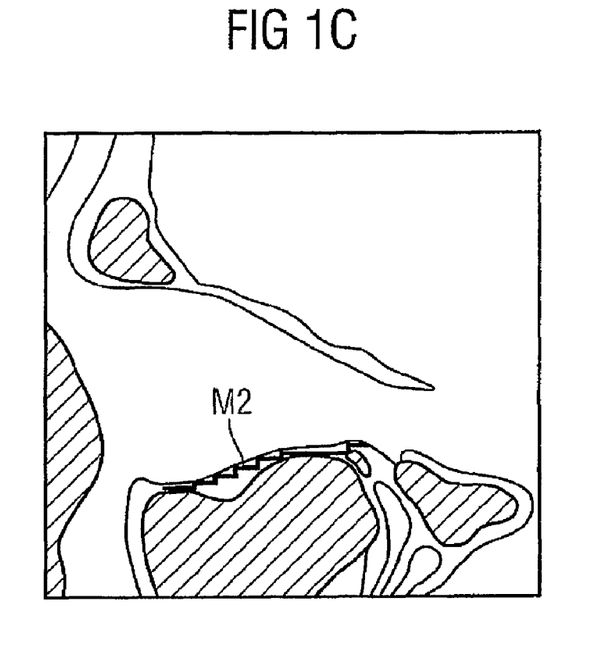
Figure 1D:
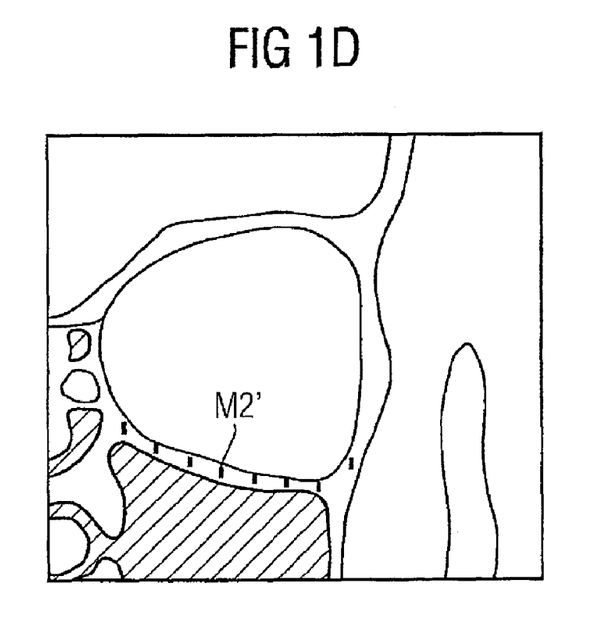

The markings M1, M2 in FIGS. 1a and 1c show the coronal as well as the sagittal marking of the bottom of the orbit as it extends in the selected layers. The layers, marked correspondingly M1' and M2', are shown in FIGS. 1b and 1d at a viewing angle, which is rotated exactly by 90°. By putting together the markings of FIGS. 1a and 1b, a three-dimensional supporting point mesh is obtained, as is explained in connection with FIGS. 2a-c.

Figure 2A:
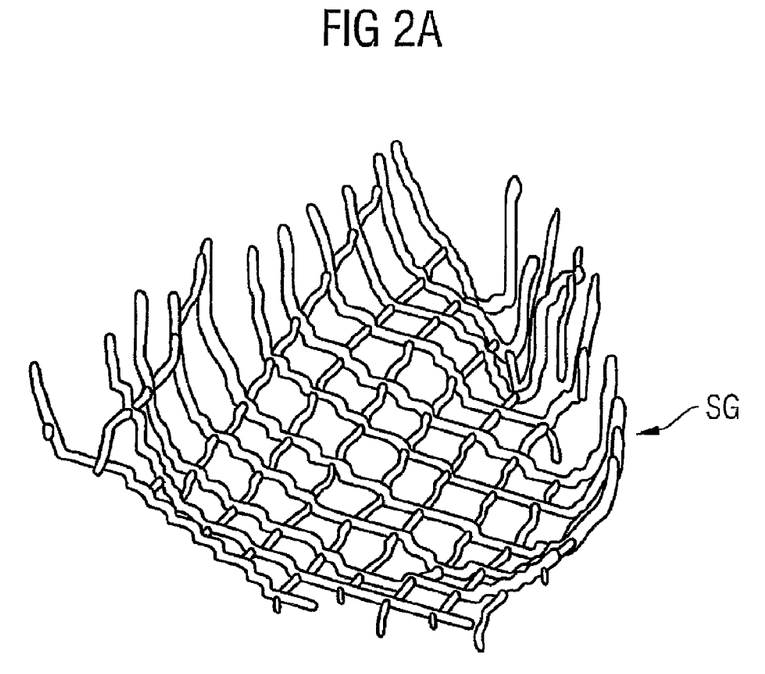
FIGS. 2*a-c* different representations of the supporting point mesh, determined for the embodiment of the inventive method for the desired anatomical shape of the implant.
Figure 2B:
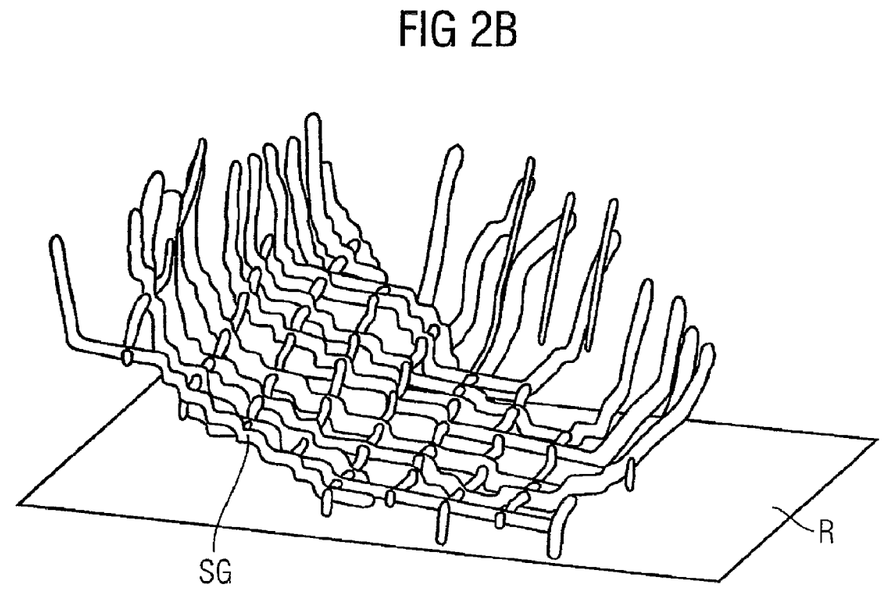
Figure 2C:
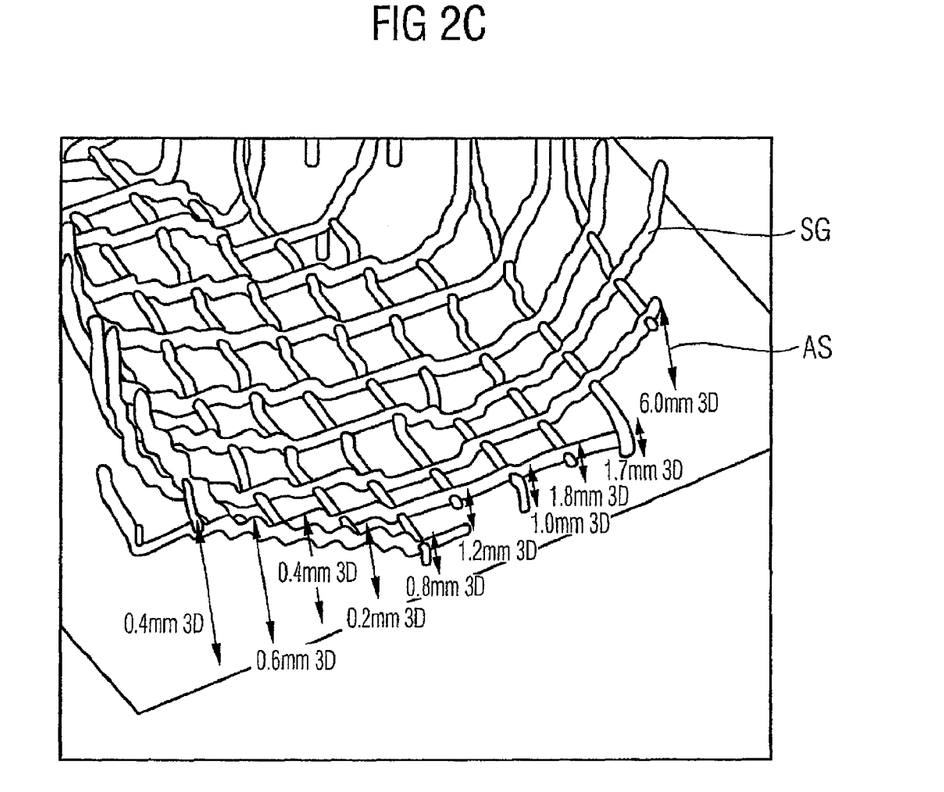

FIGS. 2a-c show different representations of the supporting point mesh, as determined for the embodiment of the inventive method, for the desired anatomical shape of the implant.

As shown in FIG. 2a, the aforementioned mirroring results in a supporting point mesh SG by viewing the coronal and sagittal layers in the three-dimensional mode. This supporting point mesh SG reflects the three-dimensional mesh profile of the desired anatomical shape of the implant, which, in this case, is the height profile of the bottom of the orbit.

Further, with regard to FIG. 2b, the ascertained supporting point mesh SG is then brought spatially into a specified orientation to a reference surface R, which corresponds to a specified reference setting of the supporting points of the preforming device. In the present case, the reference surface R is a rectangular, planar surface.

Further, with regard to FIG. 2c, the distances between the reference surface R and B. supporting point mesh at the supporting points in the reference surface is then determined for a specified orientation of the supporting point mesh.

For this purpose, perpendicular lines are simply drawn from the reference surface R to the corresponding points of the supporting point mesh, that is, there, where the supporting devices of the preforming device, which will still be explained in the following, are to rest later on.

Figure 3:
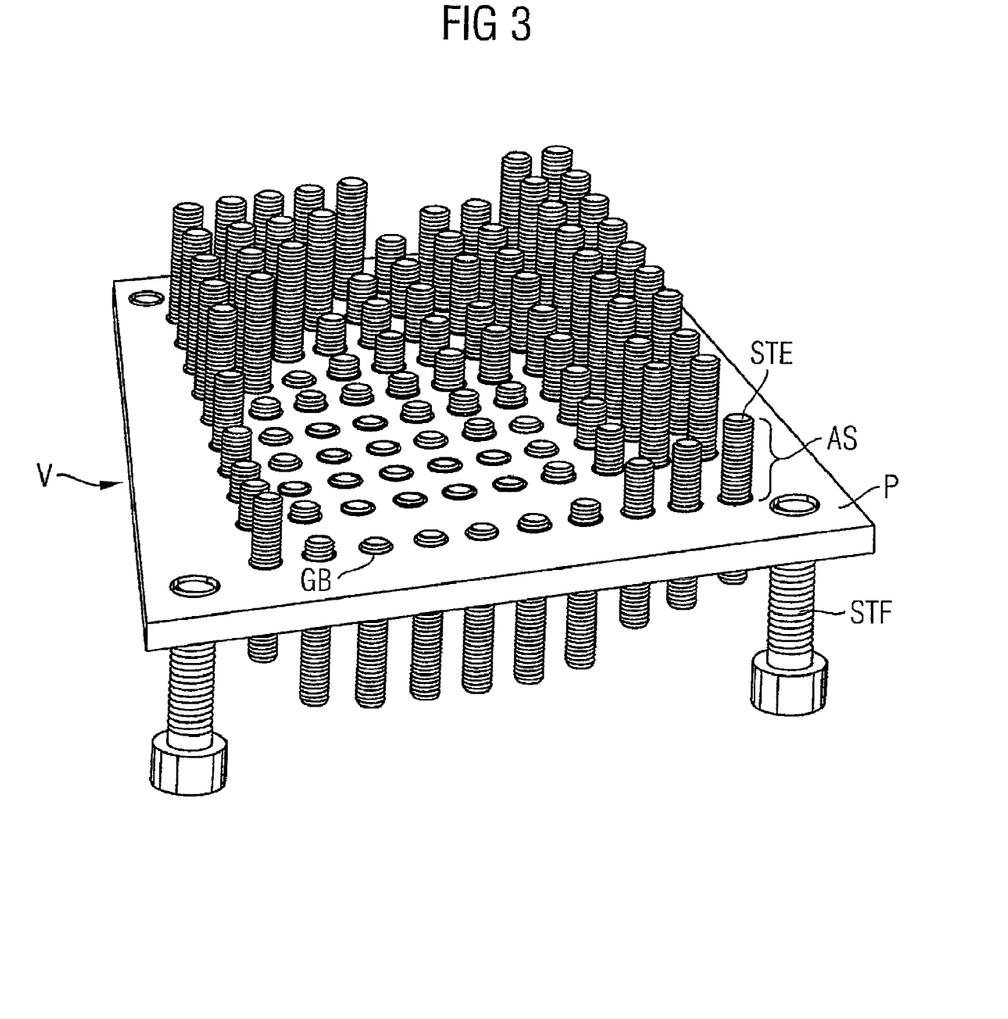
FIG. 3 shows a set preforming device for the embodiment of the inventive method.

The distances AS determined (or their relative relationships) are then identical with the settings of the supporting devices STE of the preforming device V, which is illustrated in FIG. 3.

For the present example, the preforming device V consists of a rectangular plate arrangement P, which has a rectangular matrix of threaded boreholes GB, through which the screwed-in cylinders STE, the heights of which can be adjusted, are passed. The plate device P rests on supporting feet STF, which ensure that the bottom is free for the screwed-in cylinders STE, which have been screwed in.

Once all of the distance values AS, determined according to FIG. 2c, have been converted into screw heights of the screwed-in cylinders STE, the adjustment of the preforming device V is concluded and a supporting point model of the desired anatomical structure of the implant is available.

Figure 4:
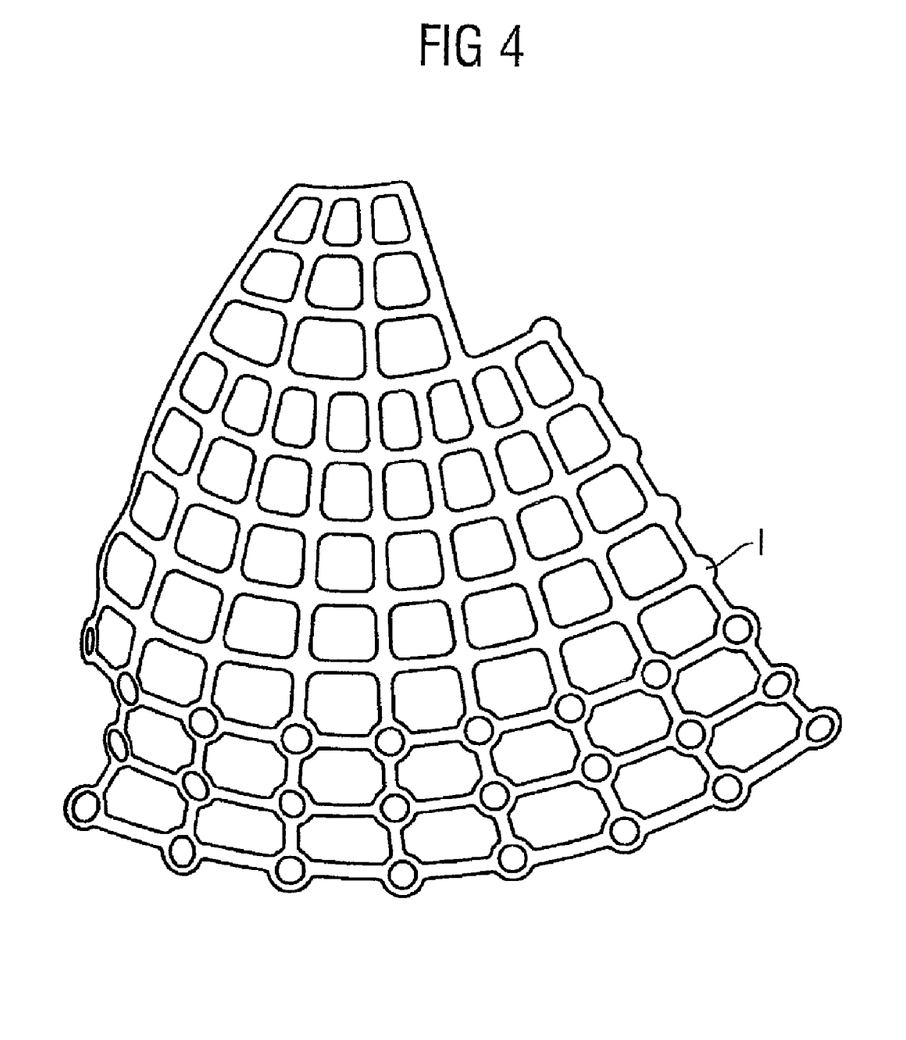
FIG. 4 shows a preformed implant for the embodiment of the inventive method.

After the adjustment of the preforming device V, the bending of the implant I takes place. To improve the configuration, a thin deformable film device or an integrally molded casing device, for example, of aluminum foil or of a rubber film or a plastic casing, may be placed on the adjusted supporting devices in the form of screwed-in cylinders STE of the preforming device V. As a result, the transitions between the supporting points are fitted better and do not have any undesirable bulges due to the contacting pressure.

After or before the implant I is bent, the edge of the implant I can be cut to size, in order to ensure that it fits exactly into the anatomical structure, which is to be operated on.

The alignment of the implant I during surgery takes place by means of the anatomical edge boundary, especially, in the present case, the front and lateral edge of the orbit, which also can be found once again easily intraoperatively.

Figure 5:
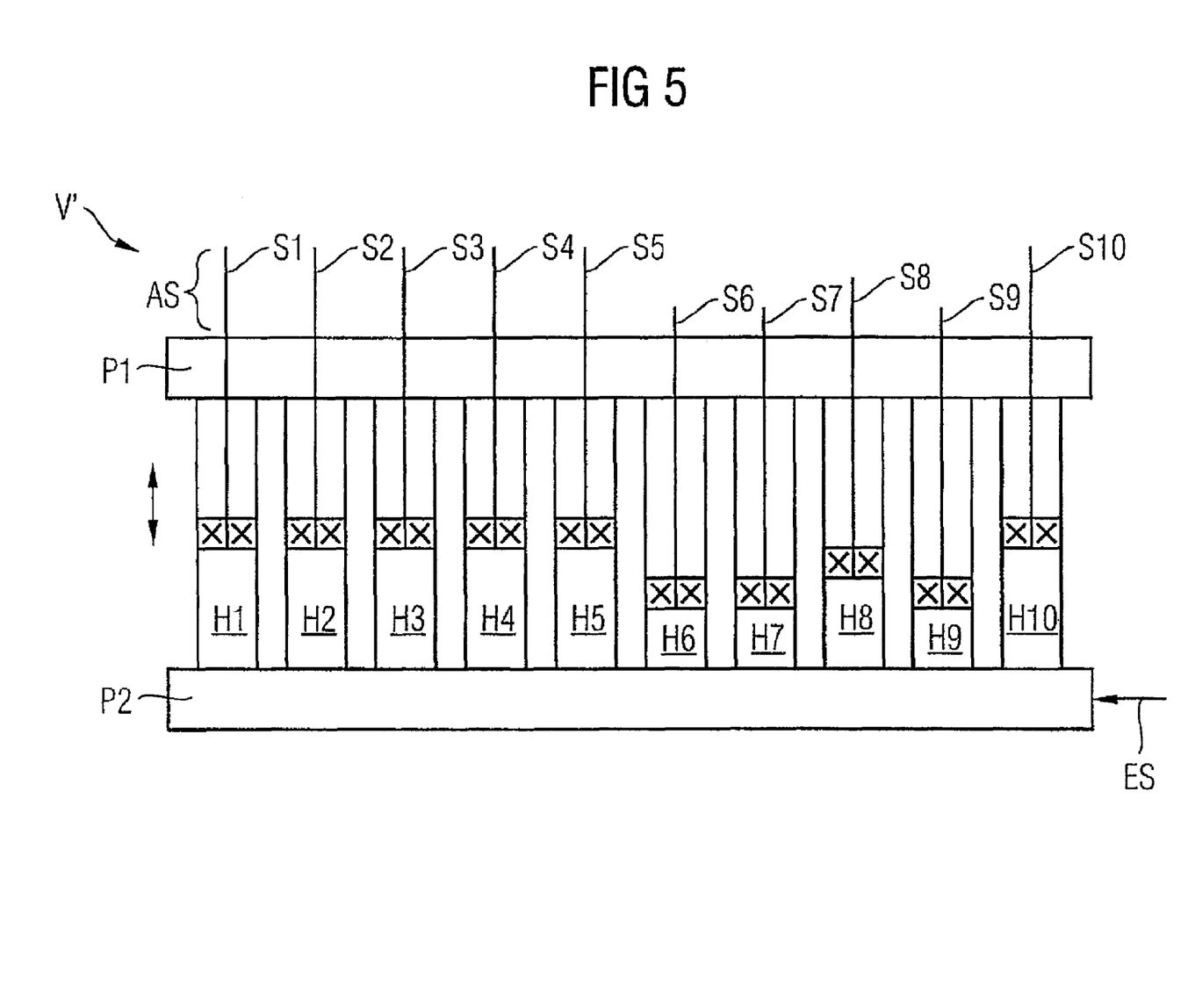
FIG. 5 shows a set preforming device for a further embodiment of the inventive method.

FIG. 5 shows a further embodiment of the preforming device V', which enables the supporting devices S1-S10, which here are thin cylindrical pins without a thread, to be adjusted automatically.

P1 and P2 in the present example refer to an upper plate device and a lower plate device. Height adjustment devices H1-H10, which set the distances AS of the supporting devices S1-S10 from the upper plate device P1, are provided between the upper plate device P1 and the lower plate device P2. In the present case, the height adjusting devices H1-H10 are electromagnetic solenoids. However, they may also be pneumatic or other mechanical height adjusting devices.

Although the present invention was described above by means of a preferred example, it is not limited to this and can be modified in various ways.

The present invention is not limited to the particular configuration of the preforming device. In particular, it is not absolutely necessary that the supporting devices all start out from a planar reference surface; instead, they may also start out from a three-dimensional reference surface if, for example, the preforming device is to be used for a highly curved, desired anatomical shape.

It is also not absolutely necessary to fix the desirable anatomic shape for each operation exactly by means of computer tomography or a similar method. Instead, once a statistically significant number of data records for the settings have been obtained, these can be stored in a database and standardized templates of the desired anatomical structure can be created. Sex, age, race, height, side of body, etc. can be provided as selection parameters.

It should also be mentioned that implants may consist of different materials, such as titanium or titanium with a coating of an absorbable, soft material, such as PDS film. In principle in any case, the present invention is not limited to the special material of the implant, as long as the material can be shaped by a bending process.

Finally, it should be mentioned that the setting of the supporting devices for the preforming device do not have to be mechanically reversible or changeable and instead, in the case of a large scale industrial production of large numbers of the same standard implant, may also be irreversible. In this case, the supporting devices can be adjusted, for example, by modeling a plastic or the like. This is particularly the case if, before the bending, a permanently integrally molded casing device is mounted on the set supporting devices of the preforming device.

Data records, made available, can also be used with the steps for configuring the preforming device for producing a flat implant, preformed to correspond to a desired anatomical shape, for a human or animal body for the purpose of shaping continuously, for example, by milling or casting.

The invention claimed is:

1. A method for producing a preformed orbital implant for a fractured orbit of a human or animal skull that also includes a healthy orbit that defines a desired anatomical shape, the method comprising the steps of:
   imaging different layers of the healthy orbit in different views so as to determine the desired anatomical shape;
   based on the determined anatomical shape, determining corresponding settings for a plurality of adjustable supporting devices of a preforming device, wherein the adjustable supporting devices define respective supporting points;
   adjusting respective positions of the supporting devices to correspond to the determined anatomical shape; and
   pressing a blank against the set supporting devices so as to bend the blank and form the preformed implant.

2. The method of claim 1, wherein the blank has a two-dimensional mesh structure, which is converted by bending the two-dimensional mesh structure into a three-dimensional mesh structure.

3. The method of claim 1, wherein the settings for the supporting devices are determined by the following steps:
   imaging the healthy orbit in a supporting point mesh;
   determining the distances between a reference surface corresponding to a specified reference setting of the supporting points of the preforming device and the supporting point mesh at the supporting points in the reference surface for a specified orientation of the supporting point mesh; and
   setting the distances determined at the supporting devices.

4. The method of claim 1, wherein the imaging of the healthy orbit into a supporting point mesh, which corresponds to the desired anatomical shape, takes place in the following steps:
   imaging the healthy orbit corresponding to a mathematical image in an image supporting point mesh; and
   transforming the image supporting point mesh into the supporting point mesh corresponding to the mathematical image.

5. The method of claim 1, wherein the imaging is carried out on a computer tomography device.

6. The method of claim 1, wherein the preformed orbital implant is a preformed osteosynthesis for the orbit.

7. The method of claim 1, wherein the supporting devices define pins, the height of which can be adjusted and which are mounted in a planar plate device.

8. The method of claim 1, further comprising the step of setting the supporting devices with a setting device based on the determined anatomical shape.

9. The method of claim 1, further comprising before the pressing step mounting a thin, deformable film device or an integrally molded casing device on the set supporting devices of the preforming device.

10. The method of claim 1, wherein the implant comprises of titanium.

11. The method of claim 1, wherein the imaging step further comprises imaging different layers of the healthy orbit in different views that are rotated 90 degrees relative to each other.

12. The method of claim 11, wherein the imaging step further comprises imaging coronal and sagittal views.

13. The method of claim 12, wherein the imaging step further comprises spacing the layers of the coronal view at a resolution that is equal to that of the sagittal view.

14. The method of claim 11, wherein the layers are spaced at a resolution of 0.5 mm.

* * * * *